United States Patent [19]

Beard

[11] 4,086,235

[45] Apr. 25, 1978

[54] 5 (6)-BENZENE RING SUBSTITUTED BENZIMIDAZOLE-2-CARBAMATE DERIVATIVES HAVING ANTHELMINTIC ACTIVITY

[75] Inventor: Colin C. Beard, Palo Alto, Calif.

[73] Assignee: Syntex (U.S.A.) Inc., Palo Alto, Calif.

[21] Appl. No.: 676,443

[22] Filed: Apr. 12, 1976

[51] Int. Cl.² .................. A61K 31/415; C07D 235/32
[52] U.S. Cl. ......................... 424/273 R; 260/558 A; 548/306; 560/16
[58] Field of Search ................. 260/309.2; 424/273; 548/306

[56] References Cited

U.S. PATENT DOCUMENTS

| 3,336,191 | 8/1967 | Craig et al. | 260/309.2 |
| 3,401,171 | 9/1968 | Craig et al. | 260/309.2 |
| 3,682,952 | 8/1972 | Actor et al. | 260/309.2 |
| 3,929,823 | 12/1975 | Beard et al. | 260/309.2 |
| 3,929,824 | 12/1975 | Beard et al. | 260/309.2 |

FOREIGN PATENT DOCUMENTS

| 2,363,351 | 7/1974 | Germany | 260/309.2 |

Primary Examiner—Natalie Trousof
Attorney, Agent, or Firm—Tom M. Moran; Joseph I. Hirsch

[57] ABSTRACT

Benzene ring substituted benzimidazole-2-carbamate derivatives represented by the formula:

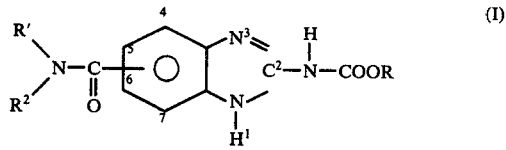

where R is a lower alkyl group having 1 to 4 carbon atoms; R' is lower alkyl having 1 to 6 carbon atoms, cycloalkyl having 3 to 7 carbon atoms, lower alkenyl or lower alkynyl having 3 to 6 carbon atoms, or phenyl; $R^2$ is hydrogen or R'; the $R'R^2NC(O)$- substitution being at the 5(6)-position; and the pharmaceutically acceptable salts thereof.

The compounds are useful as pesticides, particularly as anthelmintic and antifungal agents.

14 Claims, No Drawings

5(6)-BENZENE RING SUBSTITUTED BENZIMIDAZOLE-2-CARBAMATE DERIVATIVES HAVING ANTHELMINTIC ACTIVITY

FIELD OF THE INVENTION

This invention relates to novel chemical compounds. More particularly, this invention relates to novel anthelmintically active benzimidazole-2-carbamate derivatives wherein the benzene ring is substituted at the 5(6)-position.

BACKGROUND OF THE INVENTION

Anthelmintically active benzimidazole-2-carbamate derivatives either unsubstituted at the 5(6)-position or substituted with different substituents than those described and claimed herein are known in this art (for example, see U.S. Pat. Nos. 3,574,845; and 3,682,952). Other anthelmintically active compounds, having a different substituent at the 2-position, are also known in this art (for example, see Great Britain Pat. No. 1,122,957).

SUMMARY OF THE INVENTION

The novel benzene ring substituted benzimidazole-2-carbamate derivatives of the present invention can be represented by the following formula:

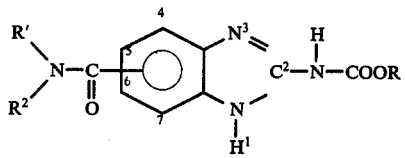 (I)

where R is a lower alkyl group having 1 to 4 carbon atoms; R' is lower alkyl having 1 to 6 carbon atoms, cycloalkyl having 3 to 7 carbon atoms, lower alkenyl or lower alkynyl having 3 to 6 carbon atoms, or phenyl; $R^2$ is hydrogen or R'; the $R'R^2NC(O)$- substitution being at the 5(6)-position; and the pharmaceutically acceptable salts thereof.

A subgroup of the compounds of this invention is a group represented by formula (I), above, wherein
R is a lower alkyl group 1 to 4 carbon atoms;
$R^1$ is a lower alkenyl group of 3 to 6 carbon atoms or a lower alkynyl group of 3 to 6 carbon atoms;
$R^2$ is hydrogen, $R^1$, lower alkyl having 1 to 6 carbon atoms, cycloalkyl having 3 to 7 carbon atoms or phenyl;
the

substituent is at the 5(6)-position; and the pharmaceutically acceptable salts thereof.

A further subgroup is a group represented by formula (I), above, wherein $R^1$ is said lower alkenyl or said lower alkynyl and $R^2$ is hydrogen or lower alkyl.

The hydrogen on the nitrogen at the 1-position can be replaced with one of the following substituents: N-alkylcarbamoyl (such as methylcarbamoyl or n-butylcarbamoyl), N,N-dialkylcarbamoyl, N-alkoxycarbonylcarbamoyl, phenylcarbamoyl, cyano, trichloromethylthio, alkylthio, phenylthio, nitrophenylthio, alkylsulfinyl, phenylsulfinyl, alkanoyl, alkoxycarbonyl, alkoxycarbonylalkylcarbonyl, alkyl, alkenyl, benzyl, benzoyl, alkoxyalkyl, alkoxycarbonylalkyl, carboxyalkyl, hydroxy and conventional esters and ethers thereof, etc. Exemplary is a compound of formula (I) wherein the hydrogen on the nitrogen at the 1-position is replaced with n-butylcarbamoyl.

As used in this specification and claims, the term "lower alkyl" refers to both straight and branched chain alkyl groups having either a total of from 1 through 4 carbon atoms or from 1 through 6 carbon atoms, as the case may be, and thus includes primary, secondary and tertiary alkyl groups. Typical lower alkyls include, for example, methyl, ethyl, n-propyl, isopropyl, n-butyl, isobutyl, t-butyl, n-amyl, n-hexyl and the like. The term "cycloalkyl" refers to cyclic hydrocarbon groups having from 3 to 7 carbon atoms such as, for example, cyclopropyl, cyclopentyl, cyclohexyl, and the like. The term "lower alkynyl" refers to an unsaturated hydrocarbon group having from 3 to 6 carbon atoms, and a single carbon-carbon triple bond, provided also that the triple bond cannot be on the α-carbon atom. The term "lower alkenyl" refers to an unsaturated hydrocarbon group having from 3 to 6 carbon atoms, and a single carbon-carbon double bond, provided also that the double bond cannot be on the α-carbon atom. Typical alkynyl groups include, for example, 2-propynyl, 2-butynyl, and the like, and typical alkenyl groups include, for example, 2-propenyl, 2-butenyl, and the like. The term "alkoxy" refers to the group having the formula $R^5O$— wherein $R^5$ is a lower alkyl group having 1 to 6 carbon atoms. Typical alkoxy groups included, for example, methoxy, ethoxy, propoxy, t-butoxy, hexyloxy and the like. The terms "alkylthio" and "alkylsulfinyl", refer to those groups having the formula $R^5S$— and

respectively, where R is a lower alkyl group having 1 to 6 carbon atoms. The term "alkanoyl" refers to alkanoyl groups derived from carboxylic acids having 1 through 6 carbon atoms such as acetyl, propionyl, butyryl, valeryl, isovaleryl, hexanoyl and the like.

The compounds of the present invention, and the pharmaceutically acceptable salts thereof, possess broad spectrum activity against parasites of mammals (human or animal), including both mature and immature parasitic forms, as represented for example, by the genera Trichostronglylus, Haemonchus, Ostertagia, Cooperia, Nematodirus, and Stronglyoides, and specifically, for example against *Nematospiroides dubius, Hymenolepis Nana, Syphacia obvelata,* and/or *Aspiculuris tetraptera.* In particular, these compounds are found to exhibit high activity against various helminthic infections of the intestinal tract of economically important animals, coupled with low systemic toxicity to the host animal.

The compounds of the present invention are also useful as antifungal agents, particularly as systemic fungicides for controlling fungal diseases of plants of economic importance.

Where the compound has a basic moiety, the term "pharmaceutically acceptable salts" refers to those salts prepared from non-toxic inorganic or organic acids, such as those salts conventionally used in the art. Such salts include for example, salts of inorganic acids such as, for example, sulfuric, sulfonic, sulfamic, nitric, phosphoric, hydrocholoric acids and the like, and salts of organic acids such as, for example, acetic, citric, lactic, palmitic, tartaric, succinic, maleic, benzoic acids and the like. Where the compound has an acidic moiety, such salts include cation salts, such as, for example, the salts of sodium, potassium, lithium, copper, ammonium, and the like.

The amount of the compound to be administered will depend upon the actual compound utilized, and upon the weight of the animal being treated. In general, however, the daily dosage level will usually be between about 0.5 mg/kg and 100 mg/kg of body weight of the animal being treated. The active ingredient is adapted to be administered to the animal by mixing it with the diet of the animal, as with a feed mix, or formulating it with a non-toxic carrier to give anthelmintic compositions. The carrier may be an orally ingestible container for the active ingredient such as, for example, a gelatin capsule, or it may be an excipient of the kind normally used in medicaments of this character, including maize starch, terra alba, lactose, sucrose, calcium phosphate, gelatin, stearic acid, agar, pectin or the like. Examples of suitable liquid carriers are peanut oil, sesame oil and water.

A wide variety of pharmaceutical forms can be employed in those cases wherein the medicament is not admixed with the feed. Thus, if a solid carrier is used, the compound can be administered in tablet or capsule form. If a liquid carrier is used, the medicament may be in the form of a soft gelatin capsule or in a liquid suspension.

In general, the compounds of the present invention can be prepared by reacting 3,4-dinitrobenzoylchloride with an appropriate amine (e.g., diethylamine) reducing the nitro groups to afford the corresponding diamino compound. The diamino compound is then reacted with a 1,3-bis(alkoxycarbonyl)-S-alkyl isothiourea or (optionally but presently less preferred) a mono(alkoxycarbonyl)-S-alkyl isothiourea to afford the desired compound of Formula I. The above diamino compound can also be prepared by converting 4-acetamido-3-nitrobenzoic acid to 4-acetamido-3-nitrobenzoylchloride, reacting the benzoyl chloride compound so formed with an appropriate amine, hydrolyzing the resultant compound under controlled conditions to convert the acetamido group to an amino group, and then reducing the nitro group to an amino group thereby affording the 1,2-diamino-4-substituted aminocarbonylbenzene intermediate which can be reacted (as described above) to afford the corresponding compound of Formula I.

Alternatively, the diamino compound can be reacted with an appropriate amount (e.g., 2 molar equivalents) of an alkoxycarbonyl isothiocyanate (e.g., methoxycarbonyl isothiocyanate) to give the corresponding 4(5)-substituted aminocarbonyl-1,2-bis(carbalkoxythioureido)benzene compound. Cyclization of this compound, as set forth below, affords the corresponding compound of Formula I. Additionally, 3-4, diaminobenzoic acid can be reacted with a 1,3-bis-(alkoxycarbonyl)-S-alkyl isothiourea or (optionally but presently less preferred) a mono(alkoxycarbonyl)-S-alkyl isothiourea to afford 5(6)-carboxy-2-carbalkoxyaminobenzimidazole which is then reacted with an appropriate amine to afford the desired compound of Formula I.

A reaction sequence ememplifying these steps is as follows:

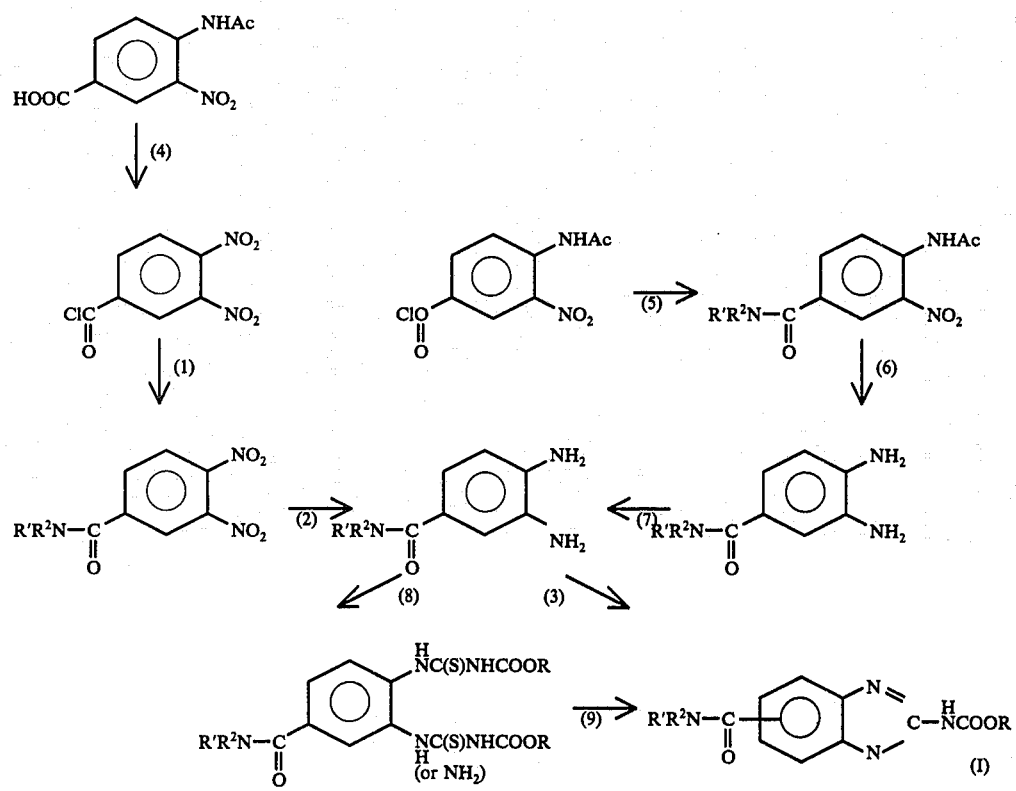

-continued

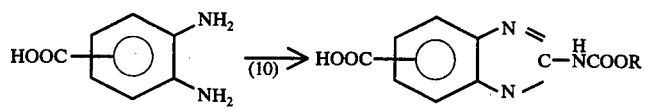

where R, R' and R² are as defined above.

The reaction of 3,4-dinitrobenzoyl chloride or 4-acetamido-3-nitrobenzoylchloride with an appropriate amine compound [such as, for example, diethylamine, dimethylamine, di(n-propyl)amine, etc.] as exemplified by steps (1) and (5) above, respectively, can be effected by reacting the benzoychloride starting material with two equivalents of the amine base (R'R²NH) or one equivalent of the amine base plus one equivalent of triethylamine in an inert solvent, such as, for example, tetrahydrofuran, bezene or methylene chloride, at about −20° C to about 80° C for about ¼ to about 24 hours. In a similar manner, the 5(6)-carboxy-2-carbalkoxyaminobenzimidazole can be reacted, as exemplified by step (11) above, with the amine base to afford the desired compound of Formula I. In this latter procedure, the 5(6)-carboxy-2-carbalkoxyaminobenzimidazole is first converted to an activated intermediate thereof, as by treatment with trifluoroacetic acid, an alkyl chloroformate or thionyl chloride, and then reacted with the heterocyclic base as set forth above.

Reduction of an nitro group to amino group, as exemplified by steps (2) and (7) above, can be effected by a variety of techniques, for example, the nitro group can be catalytically reduced utilizing hydrogen over a palladium/charcoal catalyst. This reduction is conducted in an inert solvent, such as methanol, at a temperature from about 0° to 35° C, generally about room temperature, for about ½ to about 2 hours. Other suitable inert solvents include ethyl acetate, acetic acid, and ethanol.

Another suitable reducing technique is to treat the nitro group-containing compound with stannous chloride in concentrated hydrochloric acid at a temperature in a range from about −20° C to about 100° C, generally about room temperature, for about ½ to about 6 hours. An excess of the stannous chloride reactant should be utilized, generally about 5 parts (by weight) per unit weight of the starting compound.

The reduction can also be conducted using sodium dithionite (sodium hydrosulfite) in basic aqueous methanol at reflux for 10 minutes –6 hours; by refluxing in methanol with hydrazine in the presence of a "boride" catalyst [(for example, generated from ferrous sulfate, cobalt sulfate or nickel sulfate and sodium borohydride). The latter reaction can be conducted at lower temperatures (i.e., from about 20° C to the reflux temperatures) for about ½ to 24 hours, and other alkanols (such as ethanol or propanol) can be used if desired]; or by treating the nitro-containing compound with iron powder and a ferrous salt, such as ferrous sulfate or ferrous chloride, in aqueous methanol at reflux under neutral conditions for about 1 to 24 hours, with other suitable reaction media including acetic acid or concentrated hydrochloric acid, and other suitable metals include zinc.

The diamino compounds are converted to the corresponding benzimidazole 2-carbamate compounds, as exemplified by steps (3) and (10) above, by reacting the diamino compound with a 1,3-bis(alkoxycarbonyl)-S-alkyl isothiourea, for example 1,3-bis(methoxycarbonyl)-S-methyl isothiourea or 1,3-bis(ethoxycarbonyl)-S-methyl isothiourea [or a mono(alkoxycarbonyl)-S-alkyl isothiourea or a (alkoxycarbonyl)-cyanamide, e.g., mono or bis(methoxycarbonylcyanamide], in an aqueous alcoholic medium, for example, aq. methanol or aq. ethanol, at from about room temperature to the reflux temperature of the reaction medium for about ½ to about 6 hours. The reaction medium is preferably made acidic to a pH of about 3–6 with, for example, a sufficient amount (e.g., 1–2 moles) of acetic acid or hydrochloric acid. About 1–2 moles, generally about 1.1 moles, of the isothiourea reactant are utilized per mole of the diamino compound.

4-Acetamido-3-nitrobenzoic acid is converted to the corresponding benzoyl chloride, as exemplified by step (4) above, by treatment with thionyl chloride, preferably in our inert solvent such as methylene chloride, chloroform benzene or toluene, optionally with a catalytic amount of dimethylformamide present. The reaction is typically conducted at about 20° to about 100° C for about ½ to 24 hours.

Conversion of an acylamino group, for example, an acetamido group, to an amino group, as exemplified by step (6) above, can be effected by treating the acylamino group-containing compound with a strong acid, such as hydrochloric acid, or strong base, such as sodium hydroxide, potassium hydroxide, potassium carbonate, or sodium carbonate in aqueous methanol at about 20° to about 100° C for about ¼ hour to about 24 hours.

The conversion of the diamino compound prepared in steps 2 and 7 to the corresponding bis(carbalkoxythioureido)compound, as exemplified by step (8) above, is achieved by reacting the diamino compound with an alkoxy carbonyl isothiocyanate, such as methoxy carbonyl isothiocyanate or ethoxy carbonyl isothiocyanate, in an inert reaction medium, such as acetone, tetrahydrofuran, dioxane, or dimethylformamide. This reaction is typically conducted at a temperature from about 0° to about 60° C, generally about room temperature, for about ¼ hour to about 120 hours using an excess of the isothiocyanate reactant, generally about a two-fold excess. Cyclization of the bis(carbalkoxythioureido)-compound, as exemplified by step (9) above, is conducted with cupric acetate in a mixture of acetic acid and water. This treatment, which may also be conducted on the mono(carbalkoxythioureido)-mono-amino compound, is generally conducted at about 20° to about 120° C for about 1 to 24 hours. The 1-amino-2-nitro-5-heterocycliccarbonylbenzene resulting from step (6) can also be prepared be reacting the corresponding 5-carboxy compound or preferably the acid anhydride or acid halide thereof with a heterocyclic base, for example, as set forth above with regard to steps (1) and (5).

In each of the process steps, described herein above and below, unless otherwise indicated, the respective intermediate products are not separated from the reaction mixtures. If desired, however, they can be separated and purified prior to their use as starting materials for the next step in the process. Such separation and purification can be effected by any suitable procedure. For example, typical separation procedures include filtration, extraction, evaporation, and typical purification procedures include crystallization, and both thin-layer and column chromatography. Optimum separation and isolation procedures can be obtained for any given step by routine experimentation as will be apparent to those skilled in this art.

Particular compounds falling within the scope of the present invention can be prepared by selecting an appropriate starting material, for example, from those referred to above, and then selecting particular reaction step or steps, as for example described above, to give the compound desired. In view of this disclosure, the preparation of particular compounds, including compounds falling within the scope of the present invention but not particularly described in this specification, will be apparent to those skilled in this art.

Exemplary of the compounds of the present invention, as represented by Formula I above, are the following illustrative compounds:
- 5(6)-(N,N-dimethylcarbamoyl)-2-carbomethoxyaminobenzimidazole;
- 5(6)-(N,N-diethylcarbamoyl)-2-carbomethoxyaminobenzimidazole;
- 5(6)-[N,N-di-(n-propyl)carbamoyl]-2-carbomethoxyaminobenzimidazole;
- 5(6)-[N,N-di(i-propyl)carbamoyl]-2-carbomethoxyaminobenzimidazole;
- 5(6)-(t-butylcarbamoyl)-2-carbomethoxyaminobenzimidazole;
- 5(6)-(N-methyl-N-phenylcarbamoyl)-2-carbomethoxyaminobenzimidazole;
- 5(6)-[N-cyclohexyl-N-(i-propyl)carbamoyl]-2-carbomethoxyaminobenzimidazole;
- 5(6)-[N-methyl-N-(n-propyl)carbamoyl]-2-carbomethoxyaminobenzimidazole;
- 5(6)-N,N-diprop-2-ynylcarbamoyl)-2-carbomethoxyaminobenzimidazole;
- 5(6)-(N-methyl-N-prop-2-ynylcarbamoyl)-2-carbomethoxyaminobenzimidazole;
- 5(6)-(N-prop-2-ynylcarbamoyl)-2-carbomethoxyaminobenzimidazole;
- 5(6)-(N-methyl-n-prop-2-enylcarbamoyl)-2-carbomethoxyaminobenzimidazole;
- 5(6)-(N-prop-2-enylcarbamoyl)-2-carbomethoxyaminobenzimidazole;

and the corresponding 2-carbethoxyamino-, 2-carbopropoxyamino-, or 2-carbobutoxyamino-compounds.

Of the above compounds, those wherein R is methyl in formula (I) or $R^1$ and $R^2$ are both lower alkyl (e.g. ethyl) are suitable. 5(6)-(N,N-Diethylcarbamoyl)-2-carbomethoxyaminobenzimidazole is presently preferred because of the substantial activity thereof against the helminths specifically referred to above.

With regard to those compounds where R' is lower alkenyl or lower alkynyl, it may be desirable that $R^2$ is either hydrogen or alkyl for enhanced activity.

DESCRIPTION OF SPECIFIC EMBODIMENTS

The following specific description is given to enable those skilled in this art to more clearly understand and practice the present invention. It should not be considered as a limitation upon the scope of the invention but merely as being illustrative and representative thereof.

PREPARATION 1

175 G. of S-methyl isothiouronium sulfate in one liter of water is cooled to 0° C and 162.5 g. of methylchloroformate added, followed by the addition of a solution of 250 g. potassium hydroxide in 750 ml. water at 0° to 5° C. The crude product is extracted into benzene, the benzene dried and evaporated, and the residue recrystallized from methanol. 1,3-Bis(methoxycarbonyl)-S-methyl isothiourea is thus obtained.

In a similar manner, substituting ethylchloroformate, propylchloroformate and butylchloroformate for the methylchloroformate, 1,3-bis(ethoxycarbonyl)-S-methyl isothiourea, 1,3-bis(propoxycarbonyl)-S-methyl isothiourea, and 1,3-bis(butoxycarbonyl)-S-methyl isothiourea are, respectively, prepared.

EXAMPLES I-VI

A solution of 17.4 g. (0.075 mol.) of 3,4 dinitrobenzoylchloride in 250 ml. of methylene chloride is treated at 0°-20° C with a solution of 11 g. (0.15 mol.) of diethylamine in 100 ml. of methylene chloride. The solution is kept at 20°-25° C for 2 hrs., the solvent is evaporated and the residue triturated with water. Recrystallization from methanol affords 4-(N,N-diethylcarbamoyl)-1,2-dinitrobenzene.

16 G. of 4-(N,N-diethylcarbamoyl)-1,2-dinitrobenzene in 340 ml. of methanol is hydrogenated for 3 hrs. at 45-50 psi in the presence of 1.7 g. of 5% palladided charcoal. The resulting solution of 1,2-diamino-4-(N,N-diethylcarbamoyl)benzene is filtered and concentrated to ~ 170 ml. 14.0 G. of 1,3-bis-methoxycarbonyl-S-methyl isothiourea, 170 ml. of water and 4 ml. of acetic acid are added to the diamine solution and the mixture is refluxed for 3 hrs. The solution is concentrated and cooled. Filtration and recrystallization from menthanolchloroform affords 5(6)-(N,N-diethylcarbamoyl)-2-carbomethoxyaminobenzimidazole (m.p. 235° C dec.).

In similar manner, substituting:
- di(n-propyl)amine;
- di(i-propyl)amine;
- N-methylaniline;
- N-(i-propyl) cyclohexylamine; or
- N-methyl-N-(n-propyl)amine;

for the diethylamine, the following compounds are prepared:
- 5(6)-[N,N-di(n-propyl)carbamoyl]-2-carbomethoxyaminobenzimidazole (m.p. 214° C dec.);
- 5(6)-[N,N-di(i-propyl)carbamoyl]-2-carbomethoxyaminobenzimidazole (m.p. 303° C dec.);
- 5(6)-(N-methyl-N-phenylcarbamoyl)-2-carbomethoxyaminobenzimidazole (m.P. 136°-140° C dec.);
- 5(6)-[N-cyclohexyl-N-(i-propyl)carbamoyl]-2-carbomethoxyaminobenzimidazole (m.p. 139° C dec.);
- 5(6)-[N-methyl-N-(n-propyl)carbamoyl]-2-carbomethoxyaminobenzimidazole (m.p. 164° C dec.); respectively.

In a similar manner, substituting 1,3-bis(ethoxycarbonyl)-S-methyl isothiourea, 1,3-bis(propoxycarbonyl)-S-methyl isothiourea, 1,3-bis(butoxycarbonyl)-S-methyl isothiourea for the 1,3-bis(methoxycarbonyl)-S-methyl isothiourea, the corresponding compounds are prepared where
R is ethyl, propyl or butyl, including, for example 5(6)-N,N-diethylcarbamoyl)-2-carbethoxyaminobenzimidazole,
5(6)-(N,N-diethylcarbamoyl)-2-carbopropoxyaminobenzimidazole,
and 5(6)-(N,N-diethylcarbamoyl)-2-carbobutoxyaminobenzimidazole.

EXAMPLE VII 1.45 G. of 5(6)-(N,N-diethylcarbamoyl)-2-carbomethoxyaminobenzimidazole is dissolved in a mixture of 2 ml. of water and 0.5 ml. of concentrated hydrochloric acid, and the resulting soultion is diluted with 100 ml. of acetone. After 6 hrs. at ~ 20° C, the product is filtered off to afford the hydrochloride salt of 5(6)-(N,N-diethylcarbamoyl)-2-carbomethoxyaminobenzimidazole.

EXAMPLE VIII-IX

2 G. of 1,2-diamino-4-(N,N-dimethylcarbamoyl)benzene (prepared according to the process of Example I using dimethylamine) in 100 ml. of acetone is reacted with 6 g. of methoxycarbonyl isothiocyanate for 24 hours at 20°-25° C. The solvent is removed by evaporation and the residue treated with water, filtered off and recrystallized from methanol to afford 1,2-bis(3-methoxycarbonyl-2-thioureido)-4-(N,N-dimethylcarbamoyl)benzene (m.p. 192°-193° C dec.).

A solution of 0.1 mol of cupric acetate monohydrate in ~ 40 parts of water is added to a solution of 0.1 mol of 1,2-bis(3-methoxycarbonyl-2-thioureido)-4-(N,N-dimethylcarbamoyl)benzene in ~ 20 parts of acetic acid. The mixture is refluxed until the reaction is complete (~ 24 hours), filtered while hot, diluted with water and neutralized with ammonia. The product is filtered off, washed with water and recrystallized from methanol to afford 5(6)-(N,N-dimethylcarbamoyl)-2-carbomethoxyaminobenzimidazole (m.p. 199° C dec.).

In similar manner using i-butylamine in place of dimethylamine, 5(6)-[N-(i-butyl)carbamoyl]-2-carbomethoxyaminobenzimidazole (m.p. > 310° C) is prepared.

In similar manner to the last paragraph of Examples I–VI, the corresponding compounds are prepared where R is ethyl, propyl or butyl.

EXAMPLE X

Four young Swiss-Webster male mice (16–20 g.) are artificially infected with 200 larvae of the species Nematospiroides dubius (roundworm) and Hymenolepis nana (tapeworm) and naturally injected with 15–40 larvae of Syphacia obvelata and Aspiculuris tetraptera (pinworms). The drug is administered in a commercial rat/mouse diet at the stated dose(s) from day 1 through day 18, the infection being introduced at day 0. The animals are sacrificed at day 18 and the parasites remaining in the entire small intestine, cecum and large bowel are counted and differentiated. The average number of each parasite remaining in each medicated group is compared to the average number remaining in the control. This comparison is expressed as percent reduction over the parasites in the control group. The data for illustrative compounds of this invention is tabulated in the Table below.

| 5(6)—$R'R^2NC(O)$—2—carbomethoxyaminobenzimidazoles | | | | | | | |
|---|---|---|---|---|---|---|---|
| | | | dose, | Test species (% reduction) | | | |
| Ex | R' | $R^2$ | ppm | Nd | Hn | So | At |
| I | $C_2H_5$ | $C_2H_5$ | 125 | 92 | 100 | 100 | 72 |
| | | | 62 | 73 | 100 | 100 | 88 |
| | | | 31 | 26 | 100 | 100 | 0 |
| VIII | $CH_3$ | $CH_3$ | 125 | 0 | 100 | 100 | 0 |
| II | n-$C_3H_7$ | n-$C_3H_7$ | 125 | 0 | 79 | 100 | 25 |
| III | i-$C_3H_7$ | i-$C_3H_7$ | 125 | 0 | 100 | 100 | 0 |
| IV | $CH_3$ | phenyl | 125 | 0 | 0 | 69 | 0 |
| XXIII | $C_2H_5$ | H | 250 | 100 | 100 | 100 | 100 |
| XXII | HC≡C—$CH_2$— | Me | 250 | 98 | 100 | 100 | 100 |
| VI | $CH_3$ | n-$C_3H_7$ | 125 | 0 | 100 | 100 | 59 |

Nd = Nematospiroides dubius
Hn = Symenolepis nana
So = Syphacia obvelata
At = Aspiculuris tetraptera

EXAMPLE XI

A formulation is prepared having the following composition:

| | |
|---|---|
| 5(6)-(N,N-diethylcarbamoyl)-2-carbomethoxyaminobenzimidazole | 30% |
| polyethylene glycol 6000 | 40% |
| Myrj 52 [polyoxy(40) stearate; a product of Atlas Chemical Co.] | 30% |

This formulation is prepared by heating the polyethylene glycol 6000 and Myrj 52 to 55°-60° C and, when completely melted, the 5(6)-(N,N-diethylcarbamoyl)-2-carbomethoxyaminobenzimidazole is added with stirring until homogeneous. The formulation is solidified by cooling and ground, without remelting of the polyethylene glycol, to a fine powder.

EXAMPLE XII

A drench powder is prepared having the following composition:

| | |
|---|---|
| The formulation of Example XI | 15.1 g. |
| Cabosil M-5 (colloidal silica; Cabot corp.) | 6.0 g. |
| Carboxymethyl cellulose (7M8-SXF) | 6.0 g. |

The comelt formulation and carboxymethyl cellulose are blended together until uniform, then the Cabosil is added, the mixture blended until once again uniform, and then finely powdered.

EXAMPLE XIII

A suspension is prepared having the following formulation:

| | |
|---|---|
| The formulation of Example XI | 7.550 g. |
| Citric acid, hydrous | 0.431 g. |
| sodium citrate | 0.868 g. |
| carboxymethyl cellulose (7M8-SXF) | 1.051 g. |
| Cabosil M-5 | 1.000 g. |
| sorbic acid | .300 g. |
| purified water | to 100.00 ml. |

The sorbic acid, citric acid and sodium citrate are added to 90 ml. of water which has been heated to 80° C. The Cabosil and carboxymethyl cellulose are then added, with stirring, until uniformly dispersed and fully hydrated. The mixture is cooled to 45° C, and the formulation of Example XI is added, with stirring, until it is uniformly dispersed. The suspension is cooled to room temperature and the balance of the water is added.

EXAMPLE XIV

A top dressing for horses is prepared having the following composition:

| | |
|---|---|
| The formulation of Example XI | 8.550 g. |
| granular sucrose | 17.450 g. |
| | 25.000 g. |
| water | 1.00 ml. |

EXAMPLE XV

A top dressing for cattle is prepared having the following composition:

| | |
|---|---|
| The formulation of Example XI | 75.52 g. |
| Soybean meal | 2196.30 g. |

If desired, the soybean meal can be replaced with alfalfa meal or corn gluten meal.

EXAMPLE XVI

A cattle feed additive is prepared having the following composition:

| | |
|---|---|
| The formulation of Example XI | 22.24 g. |
| feed excipient (Soybean meal, or corn gluten meal | 77.76 g. |
| | 100.00 g. |

EXAMPLE XVII

A cattle bolus is prepared having the following composition:

| | |
|---|---|
| The formulation of Example XI | 1.89 g. |
| Starch | 0.5–2.0 g. |
| Talc | 0.05–2.0 g. |
| Magnesium stearate | 0.05–2.0 g. |
| sodium chloride | 0.5–5.0 g. |
| lactose | 3.0–8.0 g. |

EXAMPLE XVIII

A cattle paste is prepared having the following composition:

| | |
|---|---|
| The formulation of Example XI | 6% |
| Corn oil | 85–90% |
| Antioxidant (e.g., a mixture of butylated hydroxy anisole and butylated hydroxy toluene) | 0.1–0.5% |
| Benzoic acid | 0.3% |
| Thickener (e.g., Cabosil M-5) | 6–10% |

EXAMPLE XIX

An equine paste is prepared having the following composition:

| | |
|---|---|
| The formulation of Example XI | 48% |
| Vegetable oil (e.g., corn oil) | 40–60% |
| Other fatty acid glycerides | 10–20% |
| Antioxidant (e.g., a mixture of butylated hydroxy anisole and butylated hydroxy toluene) | 0.1–0.5% |
| Benzoic acid | 0.3% |

-continued

| | |
|---|---|
| Thickener (e.g., Cabosil M-5) | 1–5% |
| | 100% |

EXAMPLE XX

An oral suspension for human use is prepared having the following composition:

| | |
|---|---|
| 5(6)-(N,N-diethylcarbamoyl)-2-carbomethoxyaminobenzimidazole | 2.5% |
| Benzoic acid | 0.3% |
| Veegum K | 3.0% |
| Citric acid | 0.4% |
| Sodium citrate | 0.8% |
| Sodium saccharin | 0.01% |
| Magnasweet 100 | 0.02% |
| Flavor | 0.03% |
| Color | 0.0025% |
| Water Q.S. | to 100% |

Benzoic acid, citric acid and saccharin citrate are dissolved in 90 ml of water which has been heated to 95°–100° C. Veegum K is added slowly and allowed to fully hydrate. The resultant suspension is cooled to room temperature and Magnasweet 100 and saccharin are added. The active drug is stirred in, color and flavor are added and the additional water added as necessary. The suspension is milled through a colloid mill to assure uniform dispersion.

EXAMPLE XXI

A tablet for human use is prepared having the following composition:

| | | |
|---|---|---|
| 5(6)-(N,N-diethylcarbamoyl)-2-carbomethoxyaminobenzimidazole | 40% | 100 mg |
| Starch | 15% | 37.5 mg |
| Magnesium stearate | 1% | 2.5 mg |
| Talc | 2% | 5.0 mg |
| Color (lake) | 0.24% | 0.6 mg |
| Lactose | 41.76% | 104.4 mg |
| | | 250.0 mg |
| Water | .08 ml | |

Half of the lactose is blended with the color lake, then the balance of lactose is added and blended. The active drug is added to the lactose blend and mixed until uniform. The starch paste is prepared, granulated, screened and dried to the desired moisture content. The dried granulation is screened, lubricants are added and mixed. Tablets are then prepared on a suitable tablet press.

EXAMPLE XXII

A solution of 2.31 g of 3,4-dinitrobenzoylchloride in 50 ml of methylene chloride is heated at 20°–25° C with 1.4 g of N-methyl-N-prop-2-yn-1-ylamine. After 1 to 2 hours the solution is washed with 5% hydrochloric acid, water and then dried over magnesium sulfate. The solvent is evaporated and residual 1,2-dinitro-4-(N-methyl-N-prop-2-yn-1-ylaminocarbonyl)benzene recrystallized from methanol.

A solution of 1 g of the above-described dinitro compound in 100 ml of methanol and 25 ml of water is treated with 2 g of iron powder and 0.5 g of ferrous sulfate heptahydrate. The mixture is refluxed until reduction is complete (~12 hours). The mixture is filtered and the filtrate concentrated under vacuum. The concentrated solution is treated with 1.1 g of 1,3 bismethoxycarbonyl-S methyl isothiourea and 0.5 ml of acetic acid and heated on the steam bath for 4 hours. The solution is then concentrated, neutralized with sodium bicarbonate solution, and the product filtered off. Purification is effected by recrystallization from aqueous methanol to afford 5(6)-(N-methyl-N-prop-2-yn-1-ylcarbamoyl)-2-carbomethoxyaminobenzimidazole (m.p. 187° C dec.).

EXAMPLES XXIII & XXIV

In similar manner to the procedure of Example I, substituting ethylamine and t-butylamine for the diethylamine, 5(6)-(N-ethylcarbamoyl)-2-carbomethoxyaminobenzimidazole (m.p. 284°–289° C dec.) and 5(6)-[N-(t-butyl)carbamoyl]-2-carbomethoxyaminobenzimidazole (m.p. 226°–228° C) are prepared, respectively.

EXAMPLES XXV–XXVII 1.24 G. of 5(6)-(N,N-diethylcarbamoyl)-2-carbomethoxyaminobenzimidazole is suspended in 25 ml of tetrahydrofuran. 1 Ml of n-butylisocyanate is added and the mixture stirred overnight (~15 hours). The solution is evaporated to dryness under vacuum and the residue recrystallized from acetone to afford 1-(n-butylcarbamoyl)-5(6)-(N,N-diethylcarbamoyl)-2-carbomethoxyaminobenzimidazole (m.p. 125° C dec.).

In similar manner substituting methylisocyanate and phenylisocyanate for the n-butylioscyanate, and recrystallizing from acetone-cyclohexane and triturating with acetone, respectively, 1-methylcarbamoyl-5(6)-(N,N-diethylcarbamoyl)-2-carbomethoxyaminobenzimidazole (m.p. 120° C dec.) and 1-phenylcarbamoyl-5(6)-(N,N-diethylcarbamoyl)-2-carbomethoxyaminobenzimidazole (m.p. 150°–160° C) are prepared, respectively.

In a further aspect of the invention, R' is lower alkyl having 1 to 6 carbon atoms, cycloalkyl having 3 to 7 carbon atoms, lower alkynyl having 3 to 6 carbon atoms, or phenyl. Presently, it is preferred that R' is alkyl and that $R^2$ is alkyl or hydrogen.

While the present invention has been described with reference to specific embodiments thereof, it should be understood by those skilled in this art that various changes may be made and equivalents may be substituted without departing from the true spirit and scope of the invention. In addition, many modifications may be made to adapt a particular situation, material or composition of matter, process, process step or steps, or then-present objective to the spirit of this invention without departing from its essential teachings.

What is claimed is:

1. A compound selected from the group of compounds represented by the formula

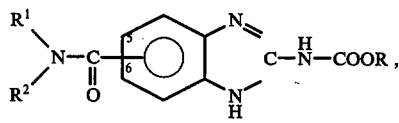

wherein
R is a lower alkyl group having 1 to 4 carbon atoms;
$R^1$ is a lower alkenyl group of 3 to 6 carbon atoms having a single carbon to carbon double bond which is not on the α-carbon atom or lower alkynyl group of 3 to 6 carbon atoms having a single carbon to carbon triple bond which is not on the α-carbon atom;
$R^2$ is hydrogen, $R^1$, lower alkyl having 1 to 6 carbon atoms, cycloalkyl having 3 to 7 carbon atoms or phenyl; the

substitution being at the 5(6)-position; and the pharmaceutically acceptable salts thereof.

2. The compound of claim 1 wherein $R^1$ is said lower alkenyl or said lower alkynyl and $R^2$ is hydrogen or lower alkyl.

3. The compound of claim 2 wherein the compound of Formula (I) is 5(6)-(N-methyl-N-prop-2-ynylcarbamoyl)-2-carbomethoxyaminobenzimidazole.

4. A compound chosen from the group consisting of 5(6)-(N,N-diethylcarbamoyl)-2-carbomethoxyaminobenzimidazole and the pharmaceutically acceptable salts thereof.

5. A compound selected from the group consisting of 5(6)-[N,N-di(isopropyl)carbamoyl]-2-carbomethoxyaminobenzimidazole and the pharmaceutically acceptable salts thereof.

6. A compound chosen from the group consisting of 5(6)-[N-(t-butyl)-carbamoyl]-2-carbomethoxyaminobenzimidazole and the pharmaceutically acceptable salts thereof.

7. A composition for controlling helminths in mammals comprising a pharmaceutically acceptable non-toxic excipient and an anthelmintically effective amount of a compound of claim 1.

8. A composition for controlling helminths in mammals comprising a pharmaceutically acceptable non-toxic excipient and an anthelmintically effective amount of a compound of claim 4.

9. A composition for controlling helminths in mammals comprising a pharmaceutically acceptable non-toxic excipient and an anthelmintically effective amount of a compound of claim 5.

10. A composition for controlling helminths in mammals comprising a pharmaceutically acceptable non-toxic excipient and an anthelmintically effective amount of a compound of claim 6.

11. The method of controlling helminths in mammals which comprises administering an anthelmintically effective amount of a compound of claim 1.

12. A method of controlling helminths in mammals which comprises administering an anthelmintically effective amount of a compound of claim 4.

13. A method of controlling helminths in mammals which comprises administering an anthelmintically effective amount of a compound of claim 5.

14. A method of controlling helminths in mammals which comprises administering an anthelmintically effective amount of a compound of claim 6.

* * * * *